United States Patent [19]

Kuroiwa et al.

[11] Patent Number: 5,115,099

[45] Date of Patent: May 19, 1992

[54] SUBSTRATES FOR DETERMINATION OF ENZYME ACTIVITY AND INTERMEDIATES FOR SYNTHESIS OF THE SUBSTRATES AS WELL AS PROCESS FOR PRODUCING THE INTERMEDIATES

[75] Inventors: Katsumasa Kuroiwa; Hitoshi Matsuura; Katsuhiro Katayama; Shuichi Nakatsuyama, all of Koriyama; Takeshi Nagasawa, Urawa; Koji Endo, Koriyama, all of Japan

[73] Assignee: Nitto Boseki Co., Ltd., Fukushima, Japan

[21] Appl. No.: 365,418

[22] Filed: Jun. 13, 1989

[30] Foreign Application Priority Data

Jun. 14, 1988 [JP] Japan ............... 63-146089
Jul. 14, 1988 [JP] Japan ............... 63-173788

[51] Int. Cl.$^5$ ............... C07K 5/08; C07K 1/06; C12Q 1/38
[52] U.S. Cl. ............... 530/331; 530/337; 435/23
[58] Field of Search ............ 530/331, 337; 514/20; 562/560; 435/23

[56] References Cited

U.S. PATENT DOCUMENTS

| | | | |
|---|---|---|---|
| 3,875,207 | 4/1975 | Iselin et al. ............... | 530/337 |
| 4,278,762 | 7/1981 | Svendsen ............... | 435/13 |
| 4,279,810 | 7/1981 | Claeson et al. ............... | 530/331 |
| 4,457,866 | 7/1984 | Karges et al. ............... | 530/331 |
| 4,480,030 | 10/1984 | Svendsen ............... | 435/23 |
| 4,508,644 | 4/1985 | Heber et al. ............... | 530/331 |
| 4,650,753 | 3/1987 | Nagasawa et al. ............... | 530/331 |
| 4,665,016 | 5/1987 | Heber et al. ............... | 530/331 |

FOREIGN PATENT DOCUMENTS 0025190 3/1981 European Pat. Off. .
0110306 6/1984 European Pat. Off. .
59-106446 6/1984 Japan .

OTHER PUBLICATIONS

Gross and Meinhofer, *The Peptides*, 1981, p. 86, Table XX.
Biochimica et Biophysica Acta, vol. 874, 1986, pp. 326-336, Elsevier Science Publishers B.V., Amsterdam, NL; R. Lottenberg et al.: "The action of factor Xa on peptide rho-nitroanilide substrates; substrate selectivity and examination of hydrolysis with different reaction conditions", p. 328, table 1.
J. Biol. Chem., 130, 81-86 (1939).
J. Gastroent, 5, 533 (1978).
Thrombosis Research, vol. 11, pp. 549-553 (1977).

*Primary Examiner*—Robert A. Wax
*Assistant Examiner*—Stephen Walsh
*Attorney, Agent, or Firm*—Darby & Darby

[57] ABSTRACT

Novel compounds represented by the following formula:

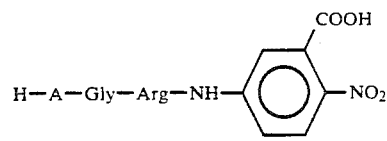

wherein A represents a specific amino acid residue are excellent as substrates for determination of enzyme activity such as trypsin, etc. The compounds can be synthesized from novel arginyl-3-tert-alkyloxycarbonyl-4-nitroanilides by a novel process comprising a selective deprotection step whereby the protecting group on the α-amine group of arginine is removed in the presence of a hydrochloric acid, acetic acid and dimethylformamide mixture, but a tert-alkyl protecting group on the —COOH group of the nitroanilide ring is not removed by this step.

6 Claims, No Drawings

SUBSTRATES FOR DETERMINATION OF ENZYME ACTIVITY AND INTERMEDIATES FOR SYNTHESIS OF THE SUBSTRATES AS WELL AS PROCESS FOR PRODUCING THE INTERMEDIATES

BACKGROUND OF THE INVENTION

1. Field of the Invention

The present invention relates to novel substrates for determination of enzyme activity which are useful for assaying enzyme activity of trypsin, $\alpha_2$-macroglobulin-trypsin complex (hereinafter simply referred to as $\alpha_2$ M-Try), or the like. The present invention also relates to intermediates for synthesis of the substrates and a process for producing the intermediates.

2. Related Art Statement

A method for determining enzyme activities of trypsin, urokinase, thrombin, etc. in human plasma involves assay using a substrate that releases a color-forming compound by the action of enzyme. According to this method, enzyme is reacted with a substrate to release a color-forming compound. An absorbance at a given wavelength that the color-forming compound absorbs is measured to determine an activity of enzyme as the analyte.

It is required that a substrate for assaying enzyme activity used in such a method should have good solubility in water or buffer, in addition to good reactivity, high selectivity, high sensitivity, high specificity to enzyme and easy detectability of its degradation products.

Many substrates have been developed heretofore as those for determination of enzyme activity. For example, proteins such as gelatin and hemoglobin, etc. have been used in the past as substrates for the detrmination of trysin. Howver, it is inappropriate to assay for trypsin activity in the pancreatic juice or duodenal juice using these substrates, since other proteinases, for example, chymotrypsin, elastase, etc., are present in such a juice.

It was reported by Bergman et al. that trypsin has the action of amidase and esterase, in addition to its proteolytic activity [J. Biol. Chem., 130, 81–86 (1939)]. Since then, many synthetic substrates (e.g., Benzyl-Arg-NH2, p-Toluenesulfonyl-Arg-OMe, Benzyl-D, L-Arg-p-Nitroanilide, p-Toluenesulfonyl-Arg-p-Nitroanilide, etc.) have been developed. However, many of these substrates cause cross reaction with serine proteases present in samples such as serum or ascitic fluid or with substances exhibiting similar enzyme activity, for example, thrombin, factor Xa, complement, kallikrein, etc. In addition, the desired reactivity with trypsin itself is insufficient so that a prolonged period of time is required for the measurement and reproducibility is questionable. Thus, these substrates cannot withstand practical use.

In recent years, arginylanilide derivatives such as Benzyloxycarbonyl-Val-Gly-Arg-p-Nitroanilide (CHR-TRY, Pentapharm Corp., U.S. Pat. No. 4,278,762), Benzyl-Ile-Glu ($\gamma$—OH and —OCH$_3$)-Gly-Arg-p-Nitroanilide.HCl (S-2222, Kabi Inc., J. Gastroent., 5, 533 (1970), Bergstrom, K), etc. have been developed as substrates for assaying trypsin activity. However, these derivatives encounter problems in selectivity, reactivity, solubility, etc. Moreover, the arginylanilide derivatives are expensive and not satisfactory yet.

In Japanese Patent Application KOKAI (Laid-Open) No. 59-106446, there are proposed color-forming substrates represented by formula:

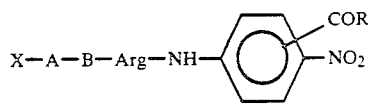

wherein X represents H or a protective group conventionally used for peptide synthesis; and A and B represent an amino acid or a residue of its derivative, as substrates for determination of enzyme activity of thrombin, kallikrein, urokinase, plasmin or the like. Substrates of ester type wherein R represents —OC$_n$H$_{2n+1}$, those of amide type wherein R represents —NHC$_n$H$_{2n+1}$ and those of amide type wherein R represents an amino acid residue are described therein; however, carboxyl type substrates wherein R represents OH are not found.

It is considered that carboxyl type substrates for determination of enzyme activity would be preferable, because of their solubility in water or buffer. It is also considered that substrates in the form of carboxyl type would exert high specificity to enzyme. Therefore, it has been desired to develop carboxyl type substrates.

SUMMARY OF THE INVENTION

An object of the present invention is to provide novel substrates for determination of enzyme activity which possess high sensitivity with and high specificity to enzyme and are excellent in solubility in water or buffer solutions and to provide easy detectability of degradation products, etc.

Another object of the present invention is to provide novel carboxyl type substrates for determination of enzyme activity which are excellent especially in solubility in water or buffer solutions and in reactivity with and specificity to enzyme.

A further object of the present invention is to provide intermediates for synthesis of novel carboxyl type substrates for determination of enzyme activity.

A still further object of the present invention is to provide a process for preparing such intermediates for synthesis.

A first aspect of the present invention is concerned with substrates for determination of enzyme activity represented by the following formula [I]:

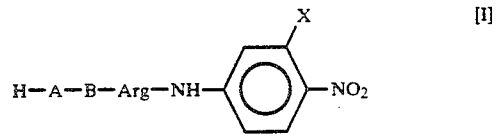

wherein A represents pyroGlu or D-Glu(OR or NR'R'') (wherein OR and NR'R'' is a group binding to r-carboxyl group of glutamic acid; R represents hydrogen, a substituted or unsubstituted alkyl of 1 to 8 carbon atoms or a substituted or unsubstituted cycloalkyl of 3 to 8 carbon atoms; R' and R'', which may be the same or different, each represents hydrogen, an alkyl of 1 to 7 carbon atoms or a cycloalkyl of 3 to 7 carbon atoms, or R' and R'' are combined together to form a cycloalkyl of 2 to 7 carbon atoms containing the nitrogen atom); B represents Gly, Pro, Pip, Sar or Ala; X represents hydrogen, carboxyl an alkoxycarbonyl of 2 to 7 carbon atoms, benzyloxycarbonyl or an alkylcarbamoyl of 2 to 7 carbon atoms; and acid addition salts thereof.

A second aspect of the present invention is concerned with arginyl-3-tert-alkyloxycarbonyl-4-nitroanilides represented by the following formula [II]:

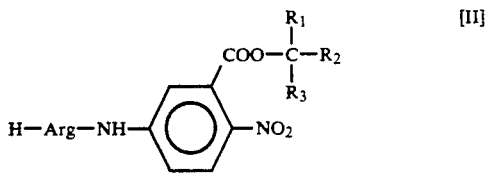

wherein each of $R_1$, $R_2$ and $R_3$ independently represents $-(CH_2)_nCH_3$ (n=0, 1, 2 or 3), and acid additionsalgts A third aspect of the present invention is concerned with a process for preparing arginyl-3-tert-alkyloxycarbonyl-4-nitroanilides represented by formula [II] and acid addition salts thereof, which comprises coupling $N\alpha$-tert-alkyloxycarbonylarginines represented by the following formula [III]:

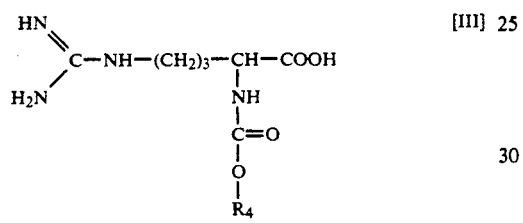

wherein $R_4$ represents a tert-alkyl of 4 to 8 carbon atoms, with tert-alkyl 5-amino-2-nitrobenzoates represented by the following formula [IV]:

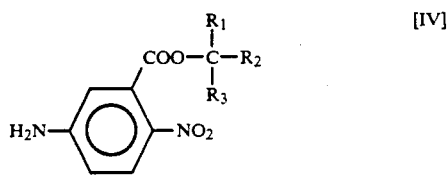

wherein $R_1$, $R_2$ and $R_3$ are as defined above, to give $N\alpha$-tert-alkyloxycarbonyl-arginyl-3-tert-alkyloxycarbonyl- 4-nitroanilides represented by the following formula [V]:

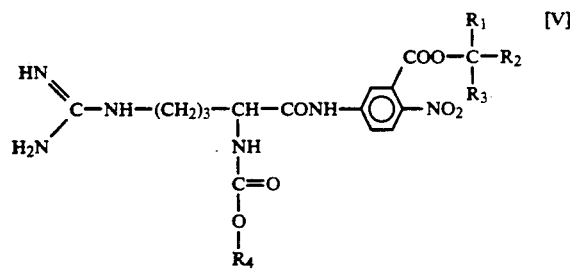

wherein $R_1$, $R_2$, $R_3$ and $R_4$ are as defined above, and then selectively splitting off the tert-alkoxycarbonyl group alone introduced as a protective group for the $\alpha$-amino group of the arginine moiety in the compound of formula V], in the presence of hydrochloric acid, acetic acid and dimethylformamide.

PREFERRED EMBODIMENTS OF THE INVENTION

Abbreviations as used in the specification are as follows.

Arg: arginine
Gly: glycine
Glu: glutaminic acid
pyroGlu: pyroglutamic acid
Pro: proline
Pip: pipecolic acid
Ala: alanine
Sar: sarcosine
Val: valine
Ile: isoleucine
Phe: phenylalanine
pNA: p-nitroaniline
ANBS: 5-amino-2-nitrobenzoic acid
Boc: tert-butyloxycarbonyl
Bzl: benzyl
$t_{Bu}$: tert-butyl
Z: benzyloxycarbonyl
WSC: water soluble carbodiimide
DCC: dicyclohexylcarbodiimide
TosOH: p-toluenesulfonic acid
Tos: p-toluenesulfonyl
DMF: dimethylformamide In formula [I] representing the present substrates for determination of enzyme activity, A represents pyroGlu or D-Glu(OR or NR'R"), preferably D-Glu(OR or NR'R"). OR or NR'R" is a group binding to $\gamma$-carboxyl group of D-glutamic acid. R represents hydrogen, a substituted or unsubstituted alkyl of 1 to 8 carbon atoms or a substituted or unsubstituted cycloalkyl of 3 to 8 carbon atoms. When R is other than hydrogen, OR forms an ester group. As the substituted or unsubstituted alkyl of 1 to 8 carbon atoms, there may be exemplified an unsubstituted alkyl of 1 to 8 carbon atoms such as methyl, n-propyl, iso-propyl, tert-butyl, pentyl-3-yl, n-hexyl, heptyl, octyl, octyl-3-yl, etc.; an alkyl of 1 to 8 carbon atoms which is substituted with a cycloalkyl of 3 to 6 carbon atoms, e.g., cyclohexylmethyl, etc.; and alkyl of 1 to 8 carbon atoms which is substituted with phenyl, e.g., benzyl (Bzl), etc. As the substituted or unsubstituted cycloalkyl of 3 to 8 carbon atoms, there may be exemplified a unsubstituted cycloalkyl of 3 to 8 carbon atoms such as cyclopentyl, cyclohexyl, cycloheptyl, cyclooctyl, etc.; a cyclohexyl substituted with an alkyl of 1 to 4 carbon atoms, such as 2-methylcyclohexyl, 3-methylcyclohexyl, 4-methylcyclohexyl, etc.; and the like.

R'0 and R", which may be the same or different, each represents hydrogen, an alkyl of 1 to 7 carbon atoms or a cycloalkyl of 3 to 7 carbon atoms, or R' and R" are combined together to form a nitrogen-containing cycloalkyl of 2 to 7 carbon atoms. In these cases, NR'R" forms an amide group. Examples of the alkyl having 1 to 7 carbon atoms include methyl, iso-propyl, n-propyl, n-hexyl, etc. Examples of the cycloalkyl having 3 to 7 carbon atoms include cycloheptyl, cyclohexyl, etc. Examples of the R' and R" being combined together to form a nitrogen-containing cycloalkyl of 2 to 7 carbon atoms include piperidino, pyrrolidino, etc.

In formula [I], B is Gly, Pro, Pip, Sar or Ala, preferably Gly.

X represents hydrogen, carboxyl, an alkoxycarbonyl of 2 to 7 carbon atoms, benzyloxycarbonyl or an alkylcarbamoyl of 2 to 7 carbon atoms. Examples of the alkoxycarbonyl having 2 to 7 carbon atoms are methoxycarbonyl, ethoxycarbonyl, propoxycarbonyl, butoxycarbonyl, pentoxycarbonyl, hexoxycarbonyl, etc. Examples of the alkylcarbamoyl of 2 to 7 carbon atoms include methylcarbamoyl, ethylcarbamoyl, propylcarbamoyl, butylcarbamoyl, pentylcarbamoyl, hexylcarbamoyl, etc.

The amino acid residue in the formula [I] is L-form, unless otherwise indicated.

The present substrates for determination of enzyme activity may be in the form of acid addition salts thereof. As such acid addition salts, there may be exemplified inorganic acid salts such as hydrochlorides, hydrobromides, phosphates, sulfates, nitrates, etc.; organic acid salts such as succinates, malates, citrates, lactates, benzenesulfonates, etc.

One of the preferred examples of the substrate in accordance with the present invention is the carboxyl type substrate of formula [I] wherein X is carboxyl and examples of such substrates include H-D-Glu(OCH.(C$_2$H$_5$)$_2$)-Gly-Arg-ANBS.2HCl[D-$\gamma$-(3-pentyloxy)glutamyl-glycyl-arginyl-3-carboxyl-4-nitroanilide dihydrochlorid], etc. Other preferred substrates are described in the examples later shown.

In the substrate of the present invention, peptide bond at the C-terminus is cleaved upon reaction with enzyme to produce a color-forming compound, p-nitroaniline or its derivative. An amount of p-nitroaniline or its derivative produced is determined based on its absorbance, whereby the desired enzyme activity can be assayed.

The characteristic feature of the present substrate for determination of enzyme activity lies in that they have excellent substrate specificity to and reactivity with enzymes such as trypsin, $\alpha_2$ M-Try, etc. and are excellent in solubility in water or buffer solutions. Examination of reactivity of the substrate u in accordance with the present invention such as D-$\gamma$-(3-pentyloxy)-glutamyl-glycyl-arginyl-3-carboxyl-4-nitroanilide dihydrochloride, etc., or CHR-TRY (Pentapharm Corp., Z-Val-Gly-Arg-pNA.HCl) and S-2222 [Kabi Inc., Bz-Ile-Glu(OR)-Gly-Arg-pNA.HCl; R=H and CH$_3$], which are known substrates, with trypsin, $\alpha_2$ M-Try and normal serum reveals that with respect to the reactivity with trypsin and $\alpha_2$ M-Try, the substrate of the present invention is almost the same as the known substrates; however, the substrate of the present invention shows a markedly reduced reactivity with normal serum, as compared to the known substrates (cf. Tables 8 and 9 later shown). Accordingly, the substrate of the present invention is extremely advantageous from the aspect of improving selectivity. The use of the substrate according to the present invention enables one to determine a trace amount of trypsin or $\alpha_2$ M-Try in a sample (e.g., serum or ascitic fluid), without diluting the sample. In addition, the substrate of the present invention has excellent solubility in water and buffer, as compared to CHR-TRY or S-2222, which enables one to prepare a substrate solution in a higher concentration than in conventional one.

As described above, the substrate of the present invention is obviously superior to the known substrates, for determination of enzyme activity of trypsin, $\alpha_2$ M-Try, etc. and thus extremely useful as a diagnostic of pancreatitis.

The substrate of the present invention represented by formula [I] can be synthesized by techniques well known in peptide chemistry.

That is, the substrate of the present invention can be synthesized by coupling p-nitroaniline or its derviatives represented by the following formula [VI]:

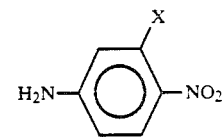

wherein X is as defined above, which correspond to the color-forming compounds produced by cleavage or degradation of the present substrate, with arginines and sequentially coupling with amino acids. Alternatively, the substrate of the present invention can also be synthesized by firstly synthesizing the N-terminal dipeptide fragment (A-B in formula [I]) and reacting the fragment with the coupling product obtained by coupling p-nitroaniline or its derviatives of formula [VI] with arginine.

In the above reaction, amino groups and carboxyl groups which are present in the molecules of the p-nitroaniline derviatives of formula [VI], amino acids, dipeptide fragment, etc. used for the reaction but do not participate directly in the reaction are protected with protective groups ordinarily used in peptide synthesis. As the amino protecting group, it is advantageous to use carbobenzoxy, tert-butyloxycarbonyl, p-methoxy, p-nitro or p-methoxyphenylazolecarbobenzoxy, phthaloyl and the like. As the carboxyl protecting group, it is advantageous to use esters of benzyl, tert-butyl, etc.

In the case of using arginine in the reaction, $\delta$-guanidino present in arginine is usually protected. For the protection, it is advantageous to use nitro or protonation.

The protective groups described above can be removed in a conventional manner, after the reaction.

Coupling of two amino acids, coupling of dipeptide fragment with amino acid, coupling of the compound of formula [VI] with arginine, etc. can be effected by the activated ester method, mixed acid anhydride method or carbodiimide method conventionally used in peptide synthesis. The activated ester method involves activation of $\alpha$-carboxyl. For the activated ester method, it is advantageous to use, for example, N-hydroxysuccinimide, p-nitrophenol, trichlorophenol, 4,6-dimethylpyrimidyl-2-thiol, etc. For the mixed acid anhydride method, the use of monoalkyl carbonates chloride, for example, isobutylchloroformate, is advantageous.

In the carbodiimide method, carbodiimides are used; it is beneficial to perform the method in the presence of, for example, N,N'-dicyclohexylcarbodiimide (DCC).

The esterification of the carboxyl at the $\gamma$-position of glutamic acid in the D-Glu(OR or NR'R") moiety of formula [I] is advantageously performed by condensation with the corresponding alcohol, for example, dehydration condensation with 3-pentanol, benzyl alcohol, etc., in the presence of an acid catalyst, or through reaction with isobutene, etc. The amidation is advantageously carried out by condensation with the corresponding amine, for example, condensation with diisopropylamine, in the presence of, e.g., dicyclohexylcarbodiimide (DCC).

According to the present invention, there are also provided arginyl-3-tert-alkyloxycarbonyl-4-nitroanilides represented by the following formula [II]:

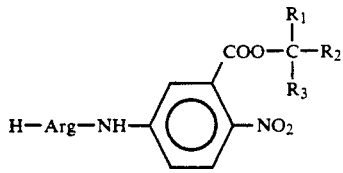

[II]

wherein each of $R_1$, $R_2$ and $R_3$ independently represents $-(CH_2)_nCH_3$ (n=0, 1, 2 or 3), and acid addition salts thereof, which are extremely useful intermediates for synthesis of carboxyl type substrates of formula [I] wherein X is carboxyl.

The carboxyl type substrate of the present invention can be prepared by coupling the compound of formula [II] with amino acids wherein the amino group is protected, in order; alternatively by coupling the compound of formula [II] with dipeptide fragment (A-B) wherein the amino group is protected, and then removing the amino protective group and carboxyl protective group formed from the 3-tert-alkyl ester group in the compound of formula [II]. The 3-tert-alkyl ester group in the compound of formula [II] can be readily hydrolyzed under mild acidic conditions. Accordingly, when the substrate of the present invention is synthesized using the compound of formula [II], the 3-tert-alkyl ester group can be easily acid-hydrolyzed, without any adverse affect like cleavage of peptide bond, etc., on the peptide produced in the synthesis and on the finally obtained substrate. Therefore, the carboxyl type substrate of the present invention can be efficiently prepared in a high yield.

In Formula [II] described above, specific examples of:

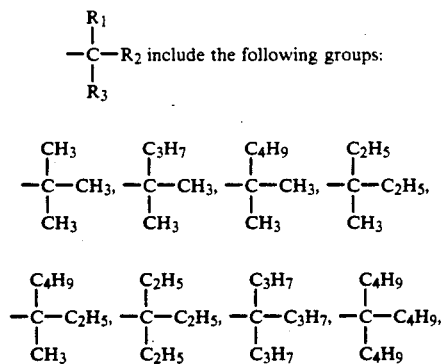

The novel compounds of formula [II] may also be in the form of acid addition salts. Examples of such acid addition salts include those described with respect to of the substrate shown by formula [I].

The compound of formula [II] or its acid addition salts in accordance with the present invention can be synthesized according to the following reaction scheme.

First step

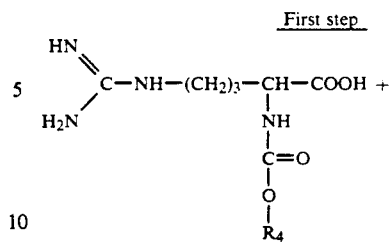

[III]

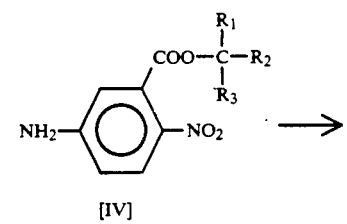

[IV]

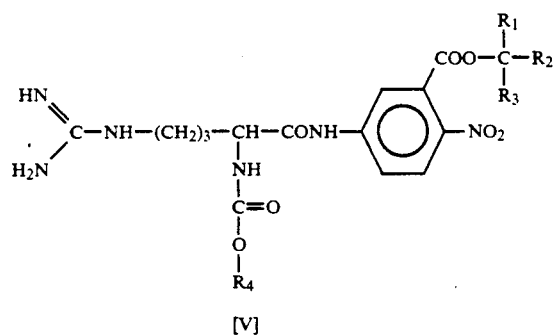

[V]

Second step
2N hydrochloric acid-acetic acid

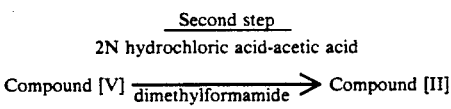

In the first step, the Nα-tert-alkyloxycarbonylarginine [III] is coupled with the tert-alkyl 5-amino- 2-nitrobenzoate [IV] according to the coupling reaction as used for the synthesis of the substrate shown by formula [I], for example, the DCC method conventionally used for peptide synthesis to give the Nα-tert-alkyloxycarbonyl-arginyl-3-tert-alkyloxycarbonyl-4-nitroanilide [V].

Subsequently, the Nα-tert-alkyloxycarbonylarginyl-3-tert-alkyloxycarbonyl-4-nitroanilide [V] is subjected to acid-hydrolysis in the second step to selectively remove the tert-alkyloxycarbonyl group alone protecting the α-amino group in the arginine moiety. A problem occurring in the step is that the conventional method for removal also causes cleavage of the tert-alkyl ester of formula [V] such as tert-butyl ester, etc. derived from the compound of formula [IV] and hence, the desired compound [II] cannot be obtained. In order to solve this problem, the present inventors have made extensive investigations and as a result, have found that by removing the protective group in the presence of hydrochloric acid, acetic acid and dimethylformamide, preferably, 2N hydrochloric acid-acetic acid-dimethylformamide (DMF), the tert-alkyloxy-carbonyl group alone that protects the α-amino group in the arginine moiety can be selectively removed.

Thus, the compound of formula [II] of the present invention can be synthesized for the first time using compounds having α-amino group in the arginine moiety protected with the tert-alkyloxycarbonyl group and containing tert-alkyl esters such as tert-alkyl ester as in the compound of formula [III] or [V], and removing the protective group under specific conditions.

Examples of the tert-alkyl shown by R: in the compounds of formula [III] or [V] include tert-butyl, 1,1-dimethylpropyl, 1,1-dimethylbutyl, 1,1-dimethylpentyl or 3-ethylpentyl-3-yl, etc.

The present invention is described in more detail by referring to the examples below but is not deemed to be limited to these examples.

In thin layer chromatography (TLC) in the examples, silica gel $F_{254}$ (manufactured by Merck) plate was used. Amino acids are all L-form, unless otherwise indicated.

EXAMPLE 1

Synthesis of arginyl-3-tert-butyloxycarbonyl-4-nitroanilide (compound of formula [II] wherein $R_1$, $R_2$ and $R_3$ are methyl)

(i) Synthesis of Nα-tert-butyloxycarbonyl-arginyl-3-tert-butyloxycarbonyl-4-nitroanilide (compound of formula [V] wherein $R_1$, $R_2$ and $R_3$ are methyl)

After 27.41 g (83.4 mmols) of Nα-tert-butyloxycarbonyl-arginine [compound of formula [III] wherein $R^4$ is tert-butyl] hydrochloride hydrate and 19.87 g (83.4 mmols) of tert-butyl 5-amino-2-nitrobenzoate (compound of formula [IV] wherein $R_1$, $R_2$ and $R_3$ are methyl) were dissolved in 167 ml of absolute pyridine, a solution of 37.86 g (183.5 mmols) of N,N'-dicyclohexylcarbodiimide in 83 ml of pyridine was dropwise added to the solution, while stirring at $-5°$ C. The resulting mixture was reacted at room temperature overnight with stirring. After completion of the reaction, 333 ml of ethyl acetate was added to the reaction solution. After the precipitated dicyclohexylurea was filtered off, the solvent was removed by distillation under reduced pressure and 750 ml of ethyl acetate was added to the residue. Insoluble matters were taken by filtration to give 37.32 g (yield, 84.3%) of Nα-tert-butyloxy- carbonyl-arginyl-3-tert-butyloxycarbonyl-4-nitroanilide.

(ii) Synthesis of arqinyl-3-tert-butyloxycarbonYl-4-nitroanilide (compound of formula [II] wherein $R_1$, $R_2$ and $R_3$ are methyl)

After 7.97 g (15 mmols) of Nα-tert-butyloxycarbonylarginyl-3-tert-butyloxycarbonyl-4-nitroanilide obtained in (i) was dissolved in 9 ml of DMF and 3 ml of acetic acid, 60 ml of 2N hydrochloride-acetic acid was added to the solution uneer ice-cooling. The resulting mixture was reacted at 15° C of a bath temperature for 30 minutes to selectively remove the Nα-protective group. After completion of the reaction, 36 ml of ethyl acetate was added to the reaction solution. The solution was poured into 2.5 liters of ether to form the precipitates. The precipitates were taken by filtration and the solvent was distilled off under reduced pressure to give 6.48 g of crude crystals. The crystals were purified through Dowex 2×8 (acetate type) [Dow Chemical] column (eluting solvent: methanol) and an equimolar amount of 0.1 N hydrochloric acid-methanol was added to the eluate. The mixture was precipitated with ether to give 5.68 g (yield, 81.0%) of the desired arginyl-3-tert-butyloxycarbonyl-4-nitroanilide dihydrochloride as crystals.

Melting point: 65°–95° C. (decomp.).

Specific rotation $[\alpha]_D^{25} = +41.5°$ (C=1, water).

The crystals gave a single spot (Rf=0.48) in silica gel thin layer chromatography (n-butanol:acetic acid:water = 4:1:2).

Elemental analysis for $C_{17}H_{28}N_6O_5Cl_2 \cdot 1/2H_2O$

Found. (%) C: 42.77 H: 6.20 N: 17.60

Calcd. (%) C: 42.86 H: 6.14 N: 17.64

EXAMPLE 2

Synthesis of H-D-Glu(OCH.$(C_2H_5)_2$)-Gly-Arg-ANBS.2HCl (Substrate No. 1)

(i) Synthesis of Boc-D-lu(OCH.$(C_2H_5)_2$)—OH

Boc-D-Glu-OBzl, 6.74 g (20 mmols), was dissolved in 20 ml of anhydrous methylene chloride. Under ice cooling, 244 mg (2 mmols) of 4-dimethylaminopyridine, 3.83 g (20 mmols) of WSC.HCl and 5.28 g (60 mmols) of 3-pentanol were added to the solution. The mixture was reacted for 5 minutes while stirring. Then, the reaction temperature was elevated to room temperature and the reaction was carried out for further 3 hours while stirring. After washing twice with 30 ml of cold 5% hydrochloric acid, twice with 30 ml of saturated sodium chloride aqueous solution, twice with 30 ml of 10% sodium hydrogencarbonate aqueous solution and then twice with 30 ml of saturated sodium chloride aqueous solution, the reaction mixture was dried over anhydrous magnesium sulfate. After drying, magnesium sulfate was filtered off and the solvent was removed by distillation under reduced pressure. The residue was purified by silica gel chromatography and recrystallized from ethyl acetate-n-hexane to give 6.51 g (80%) of Boc-D-Glu(OCH.$(C_2H_5)_2$)-OBzl.

Rf=0.68 (ethyl acetate-n-hexane = 1:3).

Elemental analysis:

Found. C: 64.64% H: 8.53% N: 3.38%.

Calcd. C: 64.84% H: 8.16% N: 3.44%.

After 6.51 g (16 mmols) of Boc-D-Glu(OCH.$(C_2H_5)_2$)-OBzl was dissolved in 200 ml of ethanol, 1 g of palladium black was added to the solution and reduction was performed at room temperature for an hour in a hydrogen flow. After the catalyst was filtered off, the solvent was removed by distillation under reduced pressure. The residue was crystallized from ethyl acetate-n-hexane to give 4.39 g (87%) of the title compound.

Rf=0.55 (CHCl$_3$:AcOH=9.5:0.5).

Elemental analysis (¼ hydrate):

Found. C: 56.07% H: 8.96% N: 4.38%.

Calcd. C: 55.97% H: 8.61% N: 4.35%.

(ii) Synthesis of Boc-D-Glu(OCH.$(C_2H_5)_2$)-Gly-OH

After 24.5 g (7.73 mmols) of Boc-D-Glu(OCH.$(C_2H_5)_2$)-OH was dissolved in 30 ml of ethyl acetate, 1.19 g (8.50 mmols) of 4,6-dimethylpyrimidyl-2-thiol was added to the solution. Under ice cooling, a solution of 1.59 g (7.73 mmols) of DCC in ethyl acetate was dropwise added to the mixture and the reaction was then carried out at room temperature overnight while stirring.

After the precipitates were filtered off, the filtrate was washed twice with 50 ml of 10% sodium hydrogencarbonate aqueous solution and twice with 50 ml of saturated sodium chloride aqueous solution followed by drying over anhydrous magnesium sulfate. After the drying agent was filtered off, the solvent was removed by distillation under reduced pressure to give 3.16 g (93%) of the activated ester.

Next, 2.66 g (11.6 mmols) of H-Gly-OBzl.TosOH was suspended in 100 ml of ethyl acetate. Under ice cooling, 1.51 ml (11.6 mmols) of N-ethylmorpholine was dropwise added to the suspension. The reaction was carried out for 5 minutes while stirring and a solution of 3.16 g (7.20 mmols) of the activated ester previously prepared in 100 ml of ethyl acetate was then added to the reaction mixture under ice cooling. The reaction was carried out overnight with stirring.

After washing twice with 150 ml of cold 5% hydrochloric acid, twice with 150 ml of saturated sodium chloride aqueous solution, twice with 150 ml of 10% sodium hydrogen-carbonate aqueous solution and then twice with 150 ml of saturated sodium chloride aqueous solution, the reaction mixture was dried and decolored over anhydrous magnesium sulfate and activated charcoal.

After the drying agent and activated charcoal were filtered off, the solvent was removed by distillation under reduced pressure. The residue was purified by silica gel chromatography to give 2.84 g (85%) of Boc-D-Glu-(OCH.$(C_2H_5)_2$)-Gly-OBzl as colorless transparent oil.

Rf=0.65 (ethyl acetate-n-hexane=1:1).
Elemental analysis:
Found. C: 61.64% H: 8.15% N: 5.96%.
Calcd. C: 62.05% H: 7.81% N: 6.03%.

After 2.84 g (6.12 mmols) of Boc-D-Glu(OCH.$(C_2H_5)_2$)-Gly-OBzl was dissolved in 200 ml of ethanol, 1 g of palladium black was added to the solution and reduction was performed at room temperature for an hour in a hydrogen flow.

After the catalyst was filtered off, the solvent was removed by distillation under reduced pressure to give 2.09 g (91%) of the title compound as oil.

Rf=0.1 (CHCl$_3$: AcOH=9.5:0.5).
Elemental analysis:
Found. C: 54.33% H: 8.29% N: 7.49%.
Calcd. C: 54.53% H: 8.08% N: 7.48%.

(iii) Synthesis of
H-D-Glyu(OCH.$(C_2H_5)_2$)-Gly-Arg-ANBS tert-butyl ester.2HCl After 2.09 g (5.59 mmols) of Boc-D-Glu(OCH.$(C_2h_5)_2$)-Gly—OH obtained in (ii) described above was dissolved in 50 ml of ethyl acetate, 861 mg (6.15 mmols) of 4,6-dimethylpyrimidyl-2-thiol was added to the solution. Under ice cooling, a solution of 1.15 g (5.59 mmols) of DCC in ethyl acetate was dropwise added to the mixture and the reaction was then carried out at room temperature overnight while stirring.

After the precipitates were filtered off, the filtrate was washed twice with 50 ml of 10% sodium hydrogencarbonate aqueoss solution and twice with 50 ml of saturated sodium chloride aqueous solution followed by drying over anhydrous magnesium sulfate.

After the drying agent was filtered off, the solvent was removed by distillation under reduced pressure to give 2.50 g (90%) of the activated ester.

Next, 2.22 g (4.75 mmols) of arginyl-3-tert-butyloxycarbonyl-4-nitroanilide obtained in Example 1 was dissolved in 20 ml of DMF. Under ice cooling, 0.62 ml (4.75 mmols) of N-ethylmorpholine was dropwise added to the solution. The reaction was carried out for 5 minutes while stirring and a solution of 2.14 g (4.32 mmols) of the previously prepared activated ester in 20 ml of DMF was then added to the reaction mixture under ice cooling. The reaction was carried out overnight with stirring. After completion of the reaction, the solvent was distilled off and 100 ml of ethyl acetate was added to the residue. After washing twice with 50 ml of cold 5% hydrochloric acid, twice with 50 ml of saturated sodium chloride aqueous solution, twice with 50 ml of 10% sodium hydrogen-carbonate aqueous solution and then twice with 50 ml of saturated sodium chloride aqueous solution, the mixture was dried over anhydrous magnesium sulfate.

After the drying agent was filtered off, the solvent was removed by distillation under reduced pressure. The residue was purified by Sephadex LH-20 chromatography to give 2.68 g (80%) of the title compound as pale yellow foam.

Rf=0.78 (chloroform:methanol:water: acetic acid=20:5:0.5:0.5).
Elemental analysis (4/5 hydrate):
Found. C: 51.19% H: 7.41% N: 13.87%.
Calcd. C: 50.94% H: 7.12% N: 13.98%.

(iv) Synthesis of
H-D-Glu(OCH.$(C_2H_5)_2$)-Gly-Arg-ANBS.2HCl

After 1.07 g (1.36 mmol) of the compound obtained in (iii) described above was dissolved in 5 ml of acetic acid, 6.8 ml (13.6 mmols) of 2N hydrochloric acid/acetic acid was dropwise added to the solution under ice cooling. The reaction was carried out for 30 minutes while stirring. Then, the reaction mixture was added to 500 ml of ether with stirring. The precipitates were filtered.

Then, the precipitates were purified by Sephadex LH-20 chromatography to give 820 mg (90%) of the desired D-r-(3-pentyloxy)-Glutamyl-Glycyl-Arginyl-3-carboxyl-4-Nitroanilide (substrate No. 1).

Rf=0.42 (n-butanol:acetic acid:water =4:1:2).
Melting point: 108°-147° C. (decomposed).
Specific rotation $[\alpha_D^{25}= -58°$ (C=1, water).
Elemental analysis (7/5 hydrate):
Found. (%) C: 43.44 H: 6.17 N: 16.13.
Calcd. (%) C: 43.34 H: 6.23 N: 16.17.

EXAMPLE 3

Novel substrates shown in Tables 1 through 7 were synthesized in a manner similar to Example 2. Physical properties of the new substrates synthesized are shown in the table below.

TABLE 1

H—D—Glu(OR)—Gly—Arg-pNA.2HCl

| Substrate No. | R | Elemental Analysis Found. (%) C H N | Elemental Analysis Calcd. (%) C H N | $[\alpha]_D^{25}$ (C, solvent) | mp. |
|---|---|---|---|---|---|
| 2 | —CH$_2$— 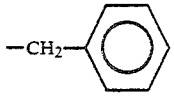 | 47.23, 5.66, 16.85 | 47.21, 5.79, 16.94 (monohydrate) | −52° (1.0, H$_2$O) | 82° C.- (decomp.) |
| 3 | —CH.(CH$_3$)$_2$ | 42.55, 6.21, 18.12 | 42.45, 6.32, 18.00 (3/2 hydrate) | −69° (1.0, H$_2$O) | 86° C.- (decomp.) |
| 4 | —(CH$_2$)$_5$.CH$_3$ | 46.51, 6.90, 16.88 | 46.44, 6.70, 17.33 (1/2 hydrate) | −56° (1.0, H$_2$O) | 81° C.- (decomp.) |
| 5 | —CH$_2$.CH.(C$_2$H$_5$).(CH$_2$)$_3$.CH$_3$ | 46.52, 6.80, 16.11 | 46.82, 7.13, 16.18 (3/2 hydrate) | −51° 1.0, H$_2$O | 91° C.- (decomp.) |
| 6 | —CH.(C$_2$H$_5$).(CH$_2$)$_4$.CH$_3$ | 45.32, 6.80, 15.70 | 45.06, 7.28, 15.57 (trihydrate) | −60° (0.1, H$_2$O) | 98° C.- (decomp.) |
| 7 | —CH$_2$— 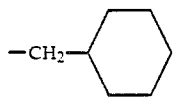 | 45.51, 6.37, 16.41 | 45.56, 6.76, 16.34 (dihydrate) | −55.8° (1.0, H$_2$O) | (98° C.- (decomp.) |
| 8 | 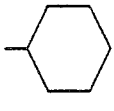 | 44.78, 6.26, 16.82 | 44.71, 6.60, 16.69 (dihydrate) | −60.5° (1.0, H$_2$O) | 158-163° C. |
| 9 | 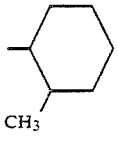 | 46.75, 6.60, 16.64 | 46.78, 6.64, 16.79 (monohydrate) | −65° (0.1, H$_2$O) | 120° C.- (decomp.) |
| 10 | 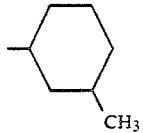 | 46.08, 6.61, 16.27 | 46.16, 6.70, 16.56 (3/2 hydrate) | −65° (0.1, H$_2$O) | 124° C.- (decomp.) |
| 11 | 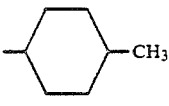 | 46.10, 6.60, 16.36 | 46.16, 6.70, 16.56 (3/2 hydrate) | −65° (0.1, H$_2$O) | 117° C.- (decomp.) |
| 12 | 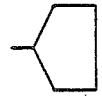 | 44.44, 6.26, 17.19 | 44.45, 6.37, 17.28 (dehydrate) | −60° (0.1, H$_2$O) | 160° C.- (decomp.) |
| 13 | 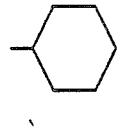 | 45.34, 6.35, 16.38 | 45.55, 6.76, 16.34 (dihydrate) | −57° (1.0, H$_2$O) | 136° C.- (decomp.) |
| 14 | 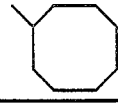 | 45.97, 6.61, 16.13 | 46.09, 6.91, 15.36 (trihydrate) | −55° (1.0, H$_2$O) | 159° C.- (decomp.) |

TABLE 2

$$\text{H}-\text{D}-\text{Glu(OR)}-\text{Gly}-\text{Arg}-\text{NH}-\underset{\text{NO}_2}{\underset{|}{\bigcirc}}-\text{CO}_2\text{H} \cdot 2\text{HCl}$$

| Substrate No. | R | Elemental Analysis Found. (%) C H N | Elemental Analysis Calcd. (%) C H N | $[\alpha]_D^{25}$ (C, solvent) | mp. |
|---|---|---|---|---|---|
| 15 | —CH₃ | 40.10, 5.49, 17.75 | 40.07, 5.45, 17.80 (monohydrate) | −90° (0.1, H₂O) | 117° C.- (decomp.) |
| 16 | —C(CH₃)₃ | 43.57, 6.12, 16.83 | 43.51, 5.93, 16.91 (1/2 hydrate) | −60° (0.1, H₂O) | 95° C.- (decomp.) |
| 17 | —cyclohexyl | 43.70, 5.99, 15.25 | 43.64, 6.20, 15.66 (dihydrate) | −70° (0.1, H₂O) | 134° C.- (decomp.) |
| 18 | —4-methylcyclohexyl | 46.76, 6.10, 16.16 | 46.70, 6.08, 16.20 (monohydrate) | −60° (0.1, H₂O) | 159° C.- (decomp.) |
| 19 | CH.(CH₃)₂.(CH₂)₂.CH₃ | 43.44, 6.17, 16.13 | 43.40, 6.18, 16.15 (monohydrate) | −α° (0.1, H₂O) | 115° C.- (decomp.) |

TABLE 3

H—D—Glu(NR'R'')—Gly—Arg-pNA.2HCl

| Substrate No. | R', R'' | Elemental Analysis Found. (%) C H N | Elemental Analysis Calcd. (%) C H N | $[\alpha]_D^{25}$ (C, solvent) | mp. |
|---|---|---|---|---|---|
| 20 | —CH(CH₃)₂ / —CH(CH₃)₂ | 45.20, 6.92, 19.01 | 45.13, 7.00, 18.94 (8/5 hydrate) | −72.5° C = 0.1, H₂O | 146–173° C. |
| 21 | —CH₂—CH₂—CH₃ / —CH₂—CH₂—CH₃ | 45.51, 7.01, 19.18 | 45.62, 6.95, 19.15 (6/5 hydrate) | −60.0° C = 0.1, H₂O | 99–145° C. |
| 22 | CH₃ / cyclohexyl | 46.62, 6.88, 18.65 | 46.60, 6.83, 18.81 (6/5 hydrate) | −60° C = 0.1, H₂O | 158–177° C. |

TABLE 4

$$\text{H}-\text{D}-\text{Glu(NR'R'')}-\text{Gly}-\text{Arg}-\text{NH}-\underset{\text{NO}_2}{\underset{|}{\bigcirc}}-\text{CO}_2\text{H} \cdot 2\text{HCl}$$

| Substrate No. | R'R'' | Elemental Analysis Found. (%) C H N | Elemental Analysis Calcd. (%) C H N | $[\alpha]_D^{25}$ (C, solvent) | mp. |
|---|---|---|---|---|---|
| 23 | —CH.(CH₃)₂ / —CH.(CH₃)₂ | 44.11, 6.59, 17.74 | 44.02, 6.56, 17.77 (8/5 hydrate) | −75° C = 0.1, H₂O | 160–180° C. |
| 24 | —CH₂—CH₂—CH₃ / —CH₂—CH₂—CH₃ | 44.13, 6.55, 17.80 | 44.02, 6.56, 17.77 (8/5 hydrate) | 60° C = 0.1, H₂O | 105–150° C. |
| 25 | CH₃ / cyclohexyl | 45.02, 6.46, 17.45 | 44.95, 6.45, 17.47 (8/5 hydrate) | −67.5° C = 0.1, H₂O | 161–177° C. |

TABLE 4-continued

H—D—Glu(NR'R")—Gly—Arg—NH—C6H3(CO2H)(NO2)·2HCl

| Substrate No. | R'R" | Found. (%) C, H, N | Calcd. (%) C, H, N | $[\alpha]_D^{25}$ (C, solvent) | mp. |
|---|---|---|---|---|---|
| 26 | –(CH2CH2)2–CH2–CH2–CH2– (pyrrolidine/piperidine ring) | 43.84, 6.14, 18.36 | 43.76, 6.08, 18.37 (6/5 hydrate) | −62.5° C = 0.1, H2O | 140–158° C. |

TABLE 5

H—D—Glu(OR)—Gly—Arg—NH—C6H3(COR5)(NO2)·2HCl

| Substrate No. | R, R5 | Found. (%) C, H, N | Calcd. (%) C, H, N | $[\alpha]_D^{25}$ (C, solvent) | mp. |
|---|---|---|---|---|---|
| 27 | R = cyclohexyl; R5 = —OCH2C6H5 | 50.29, 6.05, 14.02 | 50.03, 6.14, 14.22 (monohydrate) | −37° C = 0.5, H2O | 85–110° C. |
| 28 | R = cyclohexyl; R5 = —OCH3 | 44.09, 6.04, 15.36 | 44.45, 6.35, 15.36 (dihydrate) | −46° C = 0.5, H2O | 75–102° C. |
| 29 | R = 4-methylcyclohexyl; R5 = —OCH3 | 46.30, 6.35, 15.50 | 46.35, 6.39, 15.44 (monohydrate) | −50° C = 0.1, H2O | 80–109° C. |
| 30 | R = 4-methylcyclohexyl; R5 = —NH(CH2)3.CH3 | 48.51, 6.94, 16.49 | 48.56, 6.97, 16.44 (monohydrate) | −41° C = 0.1, H2O | 115–127° C. |
| 31 | R = —CH.(C2H5)2; R5 = —OCH3 | 44.60, 6.31, 16.03 | 44.64, 6.34, 16.02 (monohydrate) | −59° C = 0.1, H2O | 81–114° C. |
| 32 | R = —CH.(C2H5)2; R5 = —NH—(CH2)3.CH3 | 46.95, 6.90, 17.11 | 47.03, 6.94, 17.02 (monohydrate) | −45° C = 0.1, H2O | 90–109° C. |
| 33 | R = —CH.(C2H5)2; R5 = —NH.C2H5 | 45.45, 6.60, 17.73 | 45.51, 6.65, 17.69 (monohydrate) | −52° C = 0.1, H2O | 110–124° C. |

TABLE 6

H-pyroGlu—B—Arg-pNA.HCl

| Substrate No. | B | Elemental Analysis Found. (%) C H N | Elemental Analysis Calcd. (%) C H N | $[\alpha]_D^{25}$ (C, solvent) | mp. |
|---|---|---|---|---|---|
| 34 | Pip | 48.51, 6.10, 19.70 | 48.38, 6.18, 19.70 (monohydrate) | −150° C = 0.1, $H_2O$ | 138-151° C. |
| 35 | Ala | 45.07, 5.82, 21.05 | 45.24, 5.88, 21.10 (monohydrate) | −110.0° C = 0.1, $H_2O$ | 138-150° C. (decomp.) |
| 36 | Pro | 48.09, 5.89, 20.40 | 48.06, 5.90, 20.38 (3/5 hydrate) | −175.0° C = 0.1, $H_2O$ | 176-183° C. |

TABLE 7

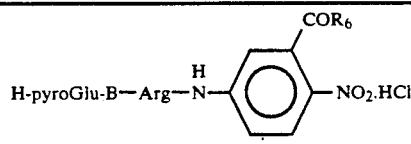

| Substrate No. | B, R6 | Elemental Analysis Found. (%) C H N | Elemental Analysis Calcd. (%) C H N | $[\alpha]_D^{25}$ (C, solvent) | mp. |
|---|---|---|---|---|---|
| 37 | B = Pro R6 = —OCH2—⌬ | 52.21, 5.77, 16.18 | 52.14, 5.69, 16.21 (monohydrate) | −111° C = 0.1, $H_2O$ | 153-180° C. |
| 38 | B = Pro R6 = —OCH3 | 46.09, 5.61, 17.39 | 45.54, 5.89, 17.71 (dihydrate) | −131° C = 0.5, $H_2O$ | 140-175° C. |
| 39 | B = Pro R6 = —OH | 45,72, 5.48, 18.45 | 45.96, 5.53, 18.64 (monohydrate) | −170.0° C = 0.1, $H_2O$ | 185-196° C. (decomp.) |
| 40 | B = Pip R6 = —OH | 47.00, 5.66, 18.04 | 46.87, 5.74, 18.22 (monohydrate) | −145° C = 0.1, $H_2O$ | 150-173° C. |
| 41 | B = Ala R6 = —OH | 43.46, 5.31, 19.16 | 43.59, 5.47, 19.37 (6/5 hydrate) | −105° C = 0.1, $H_2O$ | 152-172° C. |

EXAMPLE 4

Specificity of the synthesized new substrate was examined by reacting with each enzyme. Details of reagents used are as describved below.

(1) Substrate: 10 mM/l.

(2) Buffer: Kind of buffer, NaCl and its concentration and pH (25° C.) were set as shown below depending upon enzyme.

|  | Trypsin | $\alpha_2$-M-Try | Normal Serum |
|---|---|---|---|
| Tris (mmol) | 50 | — | 50 |
| Bistrispropane (mmol) | — | 100 | — |
| NaCl (mmol) | 150 | 150 | 150 |
| pH (25°C.) | 8.1 | 8.7 | 8.5 |

(3) Enzyme used: Enzyme used and its source, etc. are as follows.

|  | Source | Manufacturer | Lot | Unit |
|---|---|---|---|---|
| Trypsin | Bovine | Boehringer | 1073553 | 0.07 U/ml |
| $\alpha_2$ M-Try | Bovine | SIGMA (Try) | 1231-8125 |  |
|  | Bovine | Boehringer ($\alpha_2$ M) | 10357820-10 | 1/20 dilution |
| Normal serum | Human | — | — | undiluted |

(4) Terminate solution: 10% acetic acid aqueous solution.

(B) Method:

(a) Trypsin

Buffer, 0.5 ml and 0.1 ml of substrate solution are charged in a silicone-treated hard glass test tube or plastic test tube. The mixture is previously heated for 10 minutes in a thermostat at 37° C. Then, 0.05 ml of enzyme reagent is added to the mixture to perform enzyme reaction at 37° C. for 10 minutes.

Accurately 10 minutes after, 2.5 ml of the terminate solution is added to stop the enzyme reaction. Then the reaction mixture is allowed to stand at 37° C for 10 minutes and its absorbancy is measured at 405 nm.

(b) $\alpha_2$ M-Try

Buffer, 0.5 ml and 0.1 ml of substrate solution are charged in a silicone-treated hard glass test tube or plastic test tube. The mixture is previously heated for 5 minutes in a thermostat at 37° C.

Then, 0.05 ml of enzyme reagent is added to the mixture to perform enzyme reaction at 37° C. for 10 minutes.

Accurately 10 minutes after, 1.0 ml of the terminate solution is added to stop the enzyme reaction. Then the reaction mixture is allowed to stand at 37° C. for 10 minutes and its absorbancy is measured at 405 nm.

(c) Normal serum

Buffer, 0.5 ml and 0.1 ml of substrate solution are charged in a silicone-treated hard glass test tube or plastic test tube. The mixture is previously heated for 5 minutes in a thermostat at 37° C. Then, 0.1 ml of normal serum is added to the mixture to perform enzyme reaction at 37° C. for 5 minutes.

Accurately 5 minutes after, 2.0 ml of the terminate solution is added to stop the enzyme reaction. Then the reaction mixture is allowed to stand at 37° C. for 10 minutes and its absorbancy is measured at 405 nm.

The results obtained by the method described above are shown in Tables 8 through 12. Values in the tables indicate relative values when absorbancy of substrate S-2222, 10 mM, was made 1.0.

TABLE 8

H—D—Glu(OR)—Gly—Arg-pNA.2HCl

| | | Relative Reactivity to Enzyme (relative value of absorbance) | | |
|---|---|---|---|---|
| Substrate | | Try | Normal Serum | $\alpha_2$ M-Try |
| Comparative substrate: | | | | |
| | S-2222 | 1.0 | 1.0 | 1.0 |
| | S-2238 | 0.39 | 5.50 | 0.68 |
| | CHR-TRY | 0.50 | 1.70 | 0.73 |
| Substrate No. 2 | R = Bzl | 0.71 | 0.12 | 1.01 |
| Substrate No. 7 | R = —CH₂—⌬ | 0.60 | 0.28 | 0.80 |
| Substrate No. 8 | R = ⌬ | 0.86 | 0.52 | 1.24 |
| Substrate No. 3 | R = —CH(CH₃)₂ | 0.67 | 0.41 | 1.20 |
| Substrate No. 8 | R = ⌬ | 0.87 | 0.10 | 1.40 |
| Substrate No. 12 | R = ⌬ (cyclopentyl) | 0.89 | 0.43 | 1.40 |

S-2238: H—D—Phe—Pip—Arg-pNA.2HCl
[Thromb. Res., 11, 549 (1977)]

TABLE 9

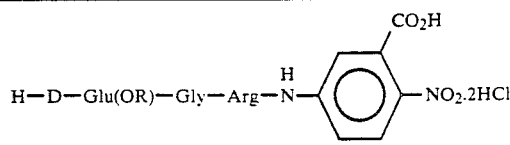

| | | Relative Reactivity to Enzyme (relative value of absorbance) | | |
|---|---|---|---|---|
| Substrate | | Try | Normal Serum | $\alpha_2$ M-Try |
| Substrate No. 16 | R = —C(CH₃)₃ | 0.38 | 0.03 | 0.44 |
| Substrate No. 17 | R = —⌬ | 0.79 | 0.07 | 1.04 |
| Substrate No. 1 | R = —CH.(C₂H₅)₂ | 0.84 | 0.03 | 1.19 |
| Substrate No. 19 | R = —CH.(CH₃).(CH₂)₂.CH₃ | 0.83 | 0.03 | 1.17 |

TABLE 9-continued

H—D—Glu(OR)—Gly—Arg—NH—C₆H₃(CO₂H)(NO₂).2HCl

| | | Relative Reactivity to Enzyme (relative value of absorbance) | | |
|---|---|---|---|---|
| Substrate | | Try | Normal Serum | $\alpha_2$ M-Try |
| Substrate No. 18 | R = ⌬—CH₃ | 0.65 | 0.13 | 0.95 |
| Substrate No. 15 | R = —CH₃ | 0.76 | 0.28 | 1.19 |

TABLE 10

H-D-Glu(NR'R")—Gly—Arg-pNA.2HCl

| | | Relative Reactivity to Enzyme (relative value of absorbance) | | |
|---|---|---|---|---|
| Substrate | | Try | Normal Serum | $\alpha_2$ M-Try |
| Substrate No. 20 | R'=R"=CH(CH₃)₂ | 0.74 | 0.20 | 1.50 |
| Substrate No. 21 | R'=R"=CH₂CH₂CH₃ | 0.74 | 0.20 | 1.46 |

TABLE 11

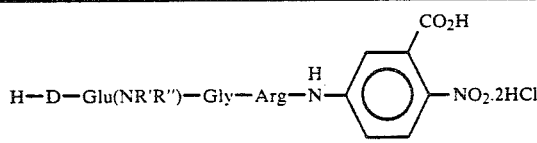

| | | Relative Reactivity to Enzyme (relative value of absorbance) | | |
|---|---|---|---|---|
| Substrate | | Try | Normal Serum | $\alpha_2$ M-Try |
| Substrate No. 23 | R' = R" = CH(CH₃)₂ | 0.66 | 0.27 | 1.12 |
| Substrate No. 24 | R' = R" = CH₂CH₂CH₃ | 0.74 | 0.10 | 1.28 |
| Substrate No. 25 | R' = CH₃, R" = ⌬ | 0.76 | 0.37 | 1.15 |
| Substrate No. 26 | R',R" = —CH₂—CH₂—CH₂—CH₂—CH₂— | 0.78 | 0.29 | 1.31 |

TABLE 12

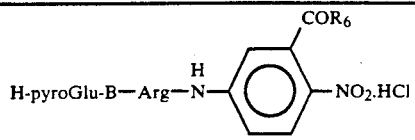

| Substrate | | Relative Reactivity to Enzyme (relative value of absorbance) | | |
|---|---|---|---|---|
| | | Try | Normal Serum | $\alpha_2$ M-Try |
| Substrate No. 40 | B = Pip<br>$R_6$ = —OH | 1.05 | 0.39 | 1.20 |
| Substrate No. 41 | B = Ala<br>$R_6$ = —OH | 1.05 | 0.08 | 1.21 |

(B) Solubility of the substrates of this invention and known substrates in water were examined. The results are shown below.

| Substrate | Solubility |
|---|---|
| S-2222: | 6 mM/l |
| CHR-TRY: | insoluble |

H—D—Glu(—O—⬡—))—Gly—Arg-pNA.2HCl:

(substrate No. 8)    more than 300 mM/l

H—D—Glu(—O—⬡—))—Gly—Arg-ANBS.2HCl:

(substrate No. 17)    more than 300 mM/l

While the invention has been described in detail and with reference to specific embodiments thereof, it will be apparent to one skilled in the art that various changes and modifications can be made therein without departing from the spirit and scope thereof.

What is claimed is:

1. A substrate for determination of enzyme activity represented by the following formula

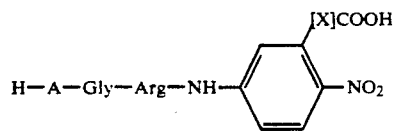

wherein A represents D-Glu(OR or NR'R"), wherein OR or NR'R" is a group binding to γ-carboxyl group of glutamic acid; R represents hydrogen, a substituted or unsuibstituted alkyl of 1 to 8 carbon atoms or a substituted or unsubstituted cycloalkyl of 3 to 8 carbon atoms; R' and R", which may be the same or different, each represents hydrogen; an alkyl of 1 to 7 carbon atoms or a cycloalkyl of 3 to 7 carbon atoms, or R' and R" are combined together to form a alkylene linkage which with the nitrogen atom form a cyclic group of 2 to 7 carbon atoms; or an acid addition salt thereof.

2. A substrate for determination of enzyme activity or an acid addition salt thereof as claimed in cliam 1, wherein A is a glutamic acid ester (D-GluOR) and R is an unsubstituted alky of 1 to 8 carbon atoms, an alkyl of 1 to 8 carbon atoms which is substituted with a cycloalkyl of 3 to 6 carbon atoms, an alkyl of 1 to 8 carbon atoms which is substituted with phenyl, an unsubstituted cycloalkyl of 3 to 8 carbon atoms, or a cyclohexyl which is substituted wtih an alkyl of 1 to 4 carbon atoms.

3. A process for preparing an arginyl-3-tert-alkyloxycarbonyl-4-nitroanilide of the following formula [II]:

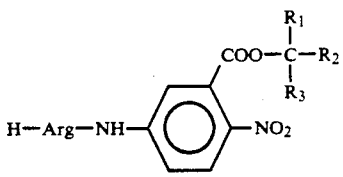

wherein each of $R_1$, $R_2$ and $R_3$ independently represents —$(CH_2)_nCH_3$ (n=0, 1, 2 or 3), and acid additionsalts thereof, which comprises coupling an Nα-tert-alkyloxycarbonylarginine represented by the following formula [III]:

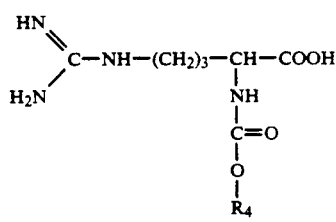

wherein $R_4$ represents a tert-alkyl of 4 to 8 carbon atoms with a tert-alkyl 5-amino-2-nitrobenzoate represented by the following formula [IV]:

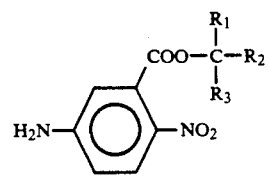

wherein R1, R2 and R3 have the same significances as described above, to give an Nα-tert-alkyloxycarbonylarginyl-3-tert-alkyloxycarbonyl-4-nitroanilide represented by the following formula [V]:

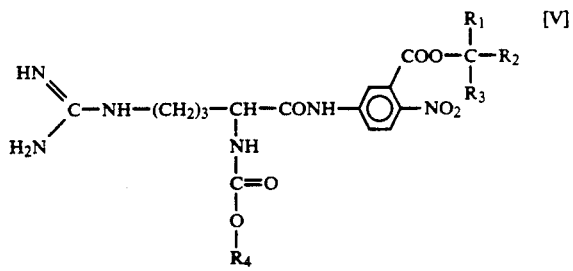

wherein $R_1$, $R_2$, $R_3$ and $R_4$ have the same significance as described above, and then selectively splitting off the tert-alkoxycarbonyl group alone introduced as a protective group for the α-amino group of the arginine moiety in said compound of formula [V], in the presence of hydrochloric acid, acetic acid and dimethylformamide.

4. A process as claimed in claim 3, wherein said hydrochloric acid is 2N hydrochloric acid.

5. A process as claimed in claim 5, wherein $R_4$ is tert-butyl.

6. The subsgtrate for the determination of enzyme activity of claim 1, wherein A represents D-Glu(OR) and R represents a substituted or unsubtituted cycloalkyl of 3 to 8 carbon atoms.

* * * * *